(12) United States Patent
Glenn

(10) Patent No.: US 8,209,015 B2
(45) Date of Patent: Jun. 26, 2012

(54) ENHANCED STABILITY IMPLANTABLE MEDICAL DEVICE

(75) Inventor: Bradley J. Glenn, Danville, CA (US)

(73) Assignee: Stealth Therapeutics, Inc., Madison, WI (US)

( * ) Notice: Subject to any disclaimer, the term of this patent is extended or adjusted under 35 U.S.C. 154(b) by 547 days.

(21) Appl. No.: 12/287,398

(22) Filed: Oct. 8, 2008

(65) Prior Publication Data

US 2009/0093765 A1 Apr. 9, 2009

Related U.S. Application Data

(60) Provisional application No. 60/960,640, filed on Oct. 9, 2007.

(51) Int. Cl.
*A61N 1/378* (2006.01)
(52) U.S. Cl. .......................................................... 607/36
(58) Field of Classification Search .................. None
See application file for complete search history.

(56) References Cited

U.S. PATENT DOCUMENTS

| | | |
|---|---|---|
| 837,085 A | 11/1906 | Loar |
| 1,434,964 A | 11/1922 | Rose |
| 1,733,189 A | 10/1929 | Friedman |
| 3,397,699 A | 8/1968 | Kohl |
| 3,692,029 A | 9/1972 | Adair |
| 3,713,447 A | 1/1973 | Adair |
| 3,938,530 A | 2/1976 | Santomieri |
| 3,951,147 A | 4/1976 | Tucker |
| 4,043,338 A | 8/1977 | Homm |
| 4,077,412 A | 3/1978 | Moossun |
| 4,543,088 A | 9/1985 | Bootman |
| 4,569,675 A | 2/1986 | Prosl |
| 4,604,090 A | 8/1986 | Reinicke |
| 4,608,965 A | 9/1986 | Anspach, Jr. |
| 4,626,244 A | 12/1986 | Reinicke |
| 4,627,838 A | 12/1986 | Cross |

(Continued)

FOREIGN PATENT DOCUMENTS

WO WO 95/12427 5/1995

OTHER PUBLICATIONS

James C. Andrews, MD et al.; Long-Term Central Venous Access with a Peripherally Placed Subcutaneous Infusion Port: Initial Results; Radiology; Jul. 1990; pp. 45-47; vol. 176, No. 1.

(Continued)

*Primary Examiner* — Carl H Layno
*Assistant Examiner* — Paula J Stice
(74) *Attorney, Agent, or Firm* — Heisler & Associates

(57) ABSTRACT

An implantable medical device is provided which has a housing of an elongate form to minimize a size of an incision required for implantation. A stabilizing element is associated with the elongated form housing for the medical device. The stabilizing element transitions from a low profile initial form to a higher width final form to provide the medical device with a stabilized footprint after implantation. The stabilizing element is in the form of a rotating wing in one embodiment. In another embodiment, the stabilizing element is in the form of an expanding loop that can bend to extend out of side openings of a cavity within the housing, to provide such stabilization at the implantation site. The medical device can be in the form of a pacemaker, infusion pump, vascular access port or other subcutaneously implanted medical device.

14 Claims, 4 Drawing Sheets

U.S. PATENT DOCUMENTS

| | | | |
|---|---|---|---|
| 4,673,394 | A | 6/1987 | Fenton, Jr. |
| 4,704,103 | A | 11/1987 | Stober |
| 4,743,231 | A | 5/1988 | Kay |
| 4,772,270 | A | 9/1988 | Wiita |
| 4,778,452 | A | 10/1988 | Moden |
| 4,802,885 | A | 2/1989 | Weeks |
| 4,880,414 | A | 11/1989 | Whipple |
| 4,995,868 | A | 2/1991 | Brazier |
| 5,090,954 | A | 2/1992 | Geary |
| 5,092,849 | A | 3/1992 | Sampson |
| 5,108,377 | A | 4/1992 | Cone |
| 5,112,310 | A | 5/1992 | Grobe |
| 5,113,846 | A | 5/1992 | Hiltebrandt |
| 5,167,638 | A | 12/1992 | Felix |
| 5,215,103 | A | 6/1993 | Desai |
| 5,217,450 | A | 6/1993 | Pryor |
| 5,217,451 | A | 6/1993 | Freitas |
| 5,275,610 | A | 1/1994 | Eberbach |
| 5,279,565 | A | 1/1994 | Klein |
| 5,306,226 | A | 4/1994 | Salama |
| 5,332,398 | A | 7/1994 | Miller |
| 5,338,297 | A | 8/1994 | Kocur |
| 5,344,439 | A | 9/1994 | Otten |
| 5,356,382 | A | 10/1994 | Picha |
| 5,360,407 | A | 11/1994 | Leonard |
| 5,365,926 | A | 11/1994 | Desai |
| 5,387,192 | A | 2/1995 | Glantz |
| 5,399,168 | A | 3/1995 | Wadsworth, Jr. |
| 5,421,832 | A | 6/1995 | Lefebvre |
| 5,443,449 | A | 8/1995 | Buelna |
| 5,454,365 | A | 10/1995 | Bonutti |
| 5,527,336 | A | 6/1996 | Rosenbluth |
| 5,547,458 | A | 8/1996 | Ortiz |
| 5,562,618 | A | 10/1996 | Cai |
| 5,624,395 | A | 4/1997 | Mikhail |
| 5,624,399 | A | 4/1997 | Ackerman |
| 5,632,729 | A | 5/1997 | Cai |
| 5,688,247 | A | 11/1997 | Haindl |
| 5,716,326 | A | 2/1998 | Dannan |
| 5,833,654 | A | 11/1998 | Powers |
| 5,848,989 | A | 12/1998 | Villani |
| 5,906,596 | A | 5/1999 | Tallarida |
| 5,957,900 | A | 9/1999 | Ouchi |
| 5,971,954 | A | 10/1999 | Conway |
| 5,989,216 | A | 11/1999 | Johnson |
| 5,990,382 | A | 11/1999 | Fox |
| 6,030,406 | A | 2/2000 | Davis |
| 6,080,142 | A | 6/2000 | Sachse |
| 6,099,506 | A | 8/2000 | Macoviak |
| 6,190,352 | B1 | 2/2001 | Haarala |
| 6,213,973 | B1 | 4/2001 | Eliasen |
| 6,355,020 | B1 | 3/2002 | Bousquet |
| 6,409,674 | B1 | 6/2002 | Brockway |
| 6,485,473 | B1 | 11/2002 | Lynn |
| 6,569,150 | B2 | 5/2003 | Teague |
| 6,572,587 | B2 | 6/2003 | Lerman |
| 6,601,795 | B1 | 8/2003 | Chen |
| 6,623,448 | B2 | 9/2003 | Slater |
| 6,629,953 | B1 | 10/2003 | Boyd |
| 6,629,956 | B1 | 10/2003 | Polidoro |
| 6,699,216 | B2 | 3/2004 | Ikeguchi |
| 6,758,831 | B2 | 7/2004 | Ryan |
| 6,780,175 | B1 | 8/2004 | Sachdeva |
| 6,893,418 | B2 | 5/2005 | Liu |
| 6,929,621 | B2 | 8/2005 | Whitmore |
| 6,997,885 | B2 | 2/2006 | Lubock |
| 6,997,909 | B2 | 2/2006 | Goldberg |
| 6,997,914 | B2 | 2/2006 | Smith |
| 7,037,321 | B2 | 5/2006 | Sachdeva |
| 7,236,829 | B1 * | 6/2007 | Farazi et al. ............ 607/36 |
| 2001/0049492 | A1 | 12/2001 | Frazier |
| 2002/0165553 | A1 | 11/2002 | Elbert |
| 2002/0177806 | A1 | 11/2002 | Meier |
| 2002/0177814 | A1 | 11/2002 | Meng |
| 2003/0014009 | A1 | 1/2003 | Kletschka |
| 2004/0078004 | A1 | 4/2004 | Bourne |
| 2004/0249342 | A1 | 12/2004 | Khosravi |
| 2004/0254537 | A1 | 12/2004 | Conlon |
| 2005/0043735 | A1 | 2/2005 | Ahmad |
| 2005/0075644 | A1 | 4/2005 | DiPoto |
| 2005/0113929 | A1 | 5/2005 | Cragg |
| 2005/0119617 | A1 | 6/2005 | Stecker |
| 2005/0131383 | A1 | 6/2005 | Chen |
| 2005/0177105 | A1 | 8/2005 | Shalev |
| 2005/0251168 | A1 | 11/2005 | Hess |
| 2006/0217673 | A1 | 9/2006 | Schulze |
| 2007/0088258 | A1 | 4/2007 | Wenchell |
| 2007/0088259 | A1 | 4/2007 | Chu |
| 2007/0276493 | A1 | 11/2007 | Malandain |

OTHER PUBLICATIONS

Ernst-Peter K. Strecker, MD et al.; Percutaneously Implantable Catheter-Port System: Preliminary Technical Results; Radiology; Feb. 1997; pp. 574-577; vol. 202, No. 2.

Hyoung II NA, MD et al.; Fixation Methods for Implantable Port Chamber: Comparative Study Using Glue, Self-Stabilizing Leg and Suture Fixations in Rabbits; Korean J Radiol 5(4); Dec. 2004, pp. 266-273.

* cited by examiner

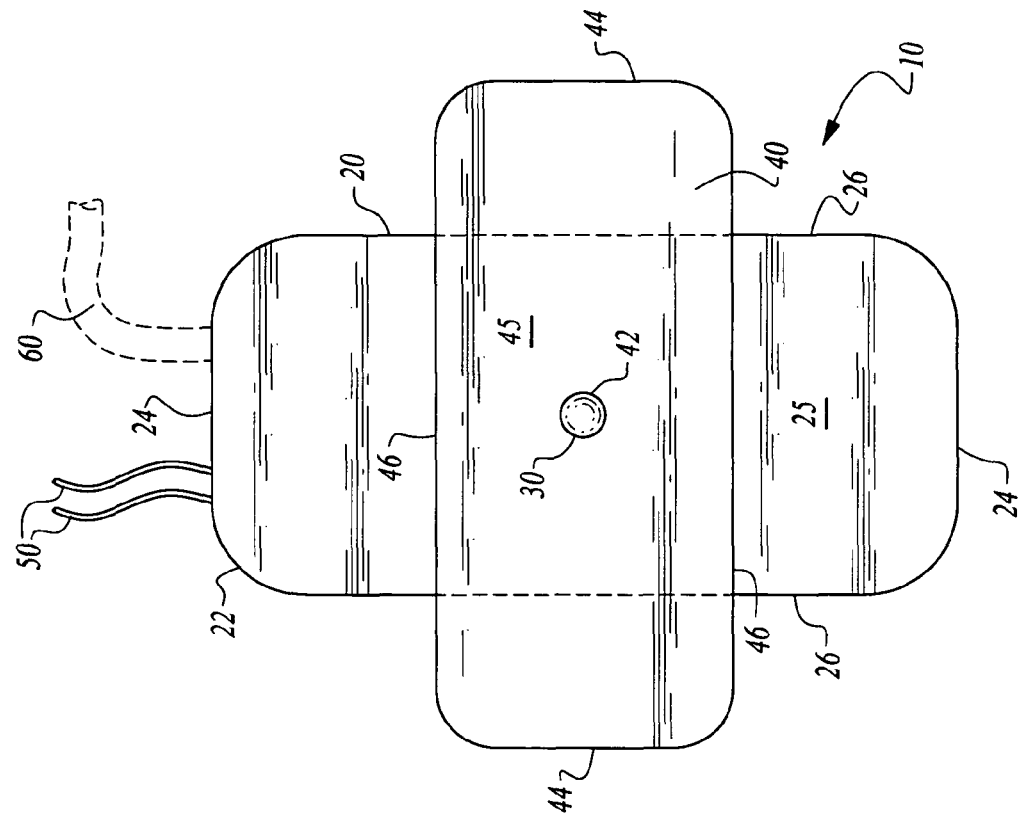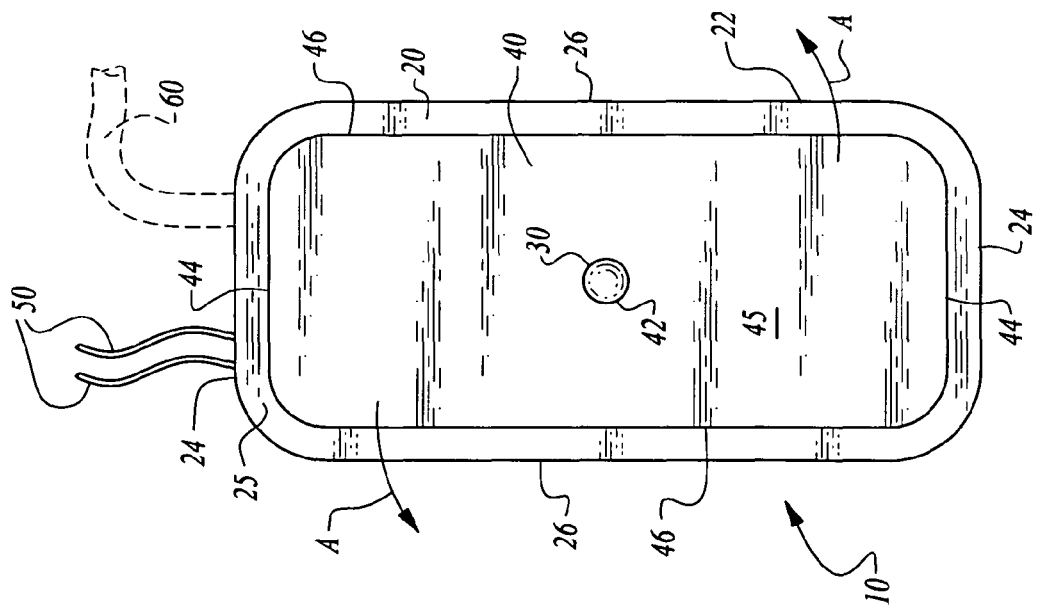

ENHANCED STABILITY IMPLANTABLE MEDICAL DEVICE

CROSS-REFERENCE TO RELATED APPLICATIONS

This application claims benefit under Title 35, United States Code §119(e) of U.S. Provisional Application No. 60/960,640 filed on Oct. 9, 2007.

This application incorporates by reference the contents of U.S. Pat. No. 7,708,722, in its entirety.

FIELD OF THE INVENTION

The following invention relates to medical devices which are implanted subcutaneously to provide a therapeutic benefit for a patient at the implantation site. More particularly, this invention relates to subcutaneously implanted medical devices which have a low profile form for minimally invasive implantation through a small incision, but which can be adjusted in form to have a highly stable configuration after implantation to resist movement after implantation. Such medical devices could be in the form of pacemakers, infusion devices, such as infusion pumps, vascular access ports, or other medical devices which are taught in the prior art to be implanted subcutaneously to provide a therapeutic benefit within a patient.

BACKGROUND OF THE INVENTION

A variety of medical conditions have been identified where implantation of a medical device is indicated. Such medical devices can include pacemakers, infusion pumps, vascular access ports, nerve stimulators, spinal stimulators, etc. Each of these medical devices generally include some form of housing which at least partially contains portions of the medical device apparatus to isolate this medical device apparatus from bodily fluids or bodily structures outside of the housing. Furthermore, typically some form of interface extends out of the housing to interact with surrounding bodily systems. For instance, in the case of a pacemaker electrodes extend from the housing as electrical leads which are coupled to nerves of the heart which, when receiving electrical stimulus from the pacemaker, cause the heart to beat. Infusion pumps include an outlet tube passing into a location where the preparation being infusion is to be delivered. For instance, if the infusion pump is infusing a pain medication, it would typically be implanted into a vascular structure, such as into a vein of the patient.

With such prior art medical devices, such implantation has required that the medical device be configured and positioned in a way that keeps the medical device stationary within the body. Such configuration has generally involved shaping the devices to be generally flat and either circular or square/rectangular in form (viewed from above). "Twiddlers Syndrome" refers to a situation where a subcutaneous medical device has been manipulated by the patient (or sometimes spontaneously) and flipped over upon itself one or more times, so that the device function is adversely affected. This can lead to fracture of output devices and potential failure of the medical device.

The shape of these medical devices requires that a relatively large incision be made to pass the medical device through the skin during surgical implantation of the medical device. As the size of the incision increases, the difficulty associated with hiding the incision from visual detection by others is increased. Generally, patients appreciate having small incisions when medical devices are to be implanted. With known prior art technology of the shape described above, such incisions have not been minimized. To some extent electronics and other components within a housing of the medical device can be miniaturized to minimize a size of the medical device and hence the required incision. However, such miniaturization has limits and other complications are associated with such miniaturization including enhanced cost and potentially reduced battery life, reduced storage capacity for medical preparations to be delivered and other potentially adverse effects. Accordingly, a need exists for a way to configure a medical device so that it can maintain fully beneficial operation while facilitating implantation through a reduced size incision. A solution to this problem would beneficially also be at least as resistant to "Twiddlers Syndrome" as prior art medical devices.

SUMMARY OF THE INVENTION

With this invention an implantable medical device is provided which can be implanted through a relatively small incision and yet maintain full stability at the implantation site. The medical device includes a housing which has an elongate form. This elongate form is defined by a long axis extending between front and rear ends thereof and a lateral axis extending between lateral sides of the housing. The long axis is longer than the lateral axis, and typically at least about twice as long as the lateral axis.

Equipment within the housing for the medical device is configured as appropriate to fit within this elongate housing, rather than in prior art housings which are generally either circular in form or rectangular/square in form. With such an elongate form, it is only necessary that an incision be provided large enough to allow the passage of the lateral cross-section of the housing, perpendicular to the long axis, to pass through the incision. For instance, if the housing is two inches long, one-half inch wide and one-half inch high, an incision of one-half inch in length (or slightly greater) is sufficient to allow passage of the housing of the medical device therethrough.

Furthermore, a stabilizing element is associated with the housing. This stabilizing element has both an elongate narrow form and a deployed wide lateral form to enhance stability of the housing and hence the entire medical device at the implantation site. This stabilizing element can be in the form of one or more wings pivotably attached to the housing. These wings have an elongate form between ends thereof with these ends aligned with the long axis of the housing during implantation. After the housing and wing have arrived at the implantation site, the wing can be rotated so that the ends thereof extend laterally away from lateral sides of the housing to stabilize the medical device. Once so stabilized, the medical device has just as much (or more) stability at the implantation site as it would have if it was not provided with this particularly elongate form. Hence, a small incision has been facilitated without any adverse impact on functionality of the medical device.

In another form, this stabilizing element is in the form of a separate loop and the housing is provided with a cavity therein with a rear opening and at least one (and preferably two) lateral side opening. The loop is routed through the rear opening and then is caused to expand within the cavity to expand out the at least one side opening to provide enhanced stability to the medical device. The loop can be bent within the cavity to extend laterally out of the side openings to stabilize the housing. Alternatively, the loop can be formed of a resilient material which is initially restrained into an elongate form aligned with the long axis of the housing, but which springs to a natural original form after passing into the cavity where portions of the loop extend out the lateral side openings of the cavity, to stabilize the housing after the loop has been inserted entirely within the cavity.

OBJECTS OF THE INVENTION

Accordingly, a primary object of the present invention is to provide a medical device which can pass through a reduced size incision while maintaining stability at an implantation site subcutaneously within the body of a patient.

Another object of the present invention is to provide a medical device which can be implanted into a subcutaneous implantation site within the body of a patient.

Another object of the present invention is to provide a method for implanting a medical device and stabilizing the medical device once implanted.

Another object of the present invention is to provide a subcutaneous implantable medical device which has a small cross-section for implantation through a small incision which maintains high stability once implanted.

Another object of the present invention is to provide a medical device which can morph between a smaller profile implantation form and a larger profile static implanted form after being implanted at an implantation site.

Another object of the present invention is to provide a pacemaker which can be implanted through a small incision and still maintain stability once implanted.

Another object of the present invention is to provide a medical device which can be stabilized after implantation with the stabilization process easily and reliably performed by a medical professional.

Other further objects of the present invention will become apparent from a careful reading of the included drawing figures, the claims and detailed description of the invention.

BRIEF DESCRIPTION OF THE DRAWINGS

FIG. 1 is a bottom plan view of an implantable medical device shown before rotation of a wing thereof to stabilize the medical device.

FIG. 2 is a bottom plan view similar to that which is shown in FIG. 1 but after rotation of the stabilizing element in the form of a wing to stabilize the medical device.

DESCRIPTION OF THE PREFERRED EMBODIMENT

Figure 3:
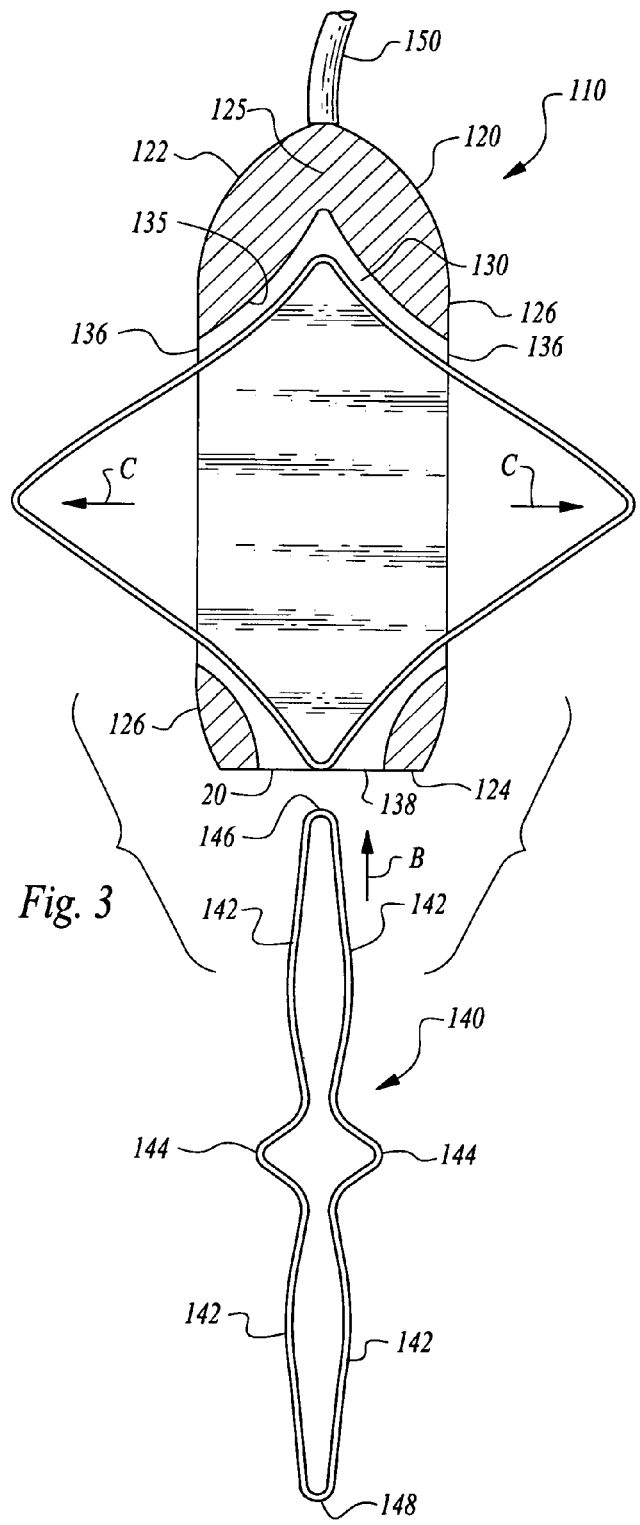
FIG. 3 is a bottom plan view of an implantable medical device having a cavity and a loop which can pass into the cavity and expand within the cavity to stabilize the housing.
Figure 4:
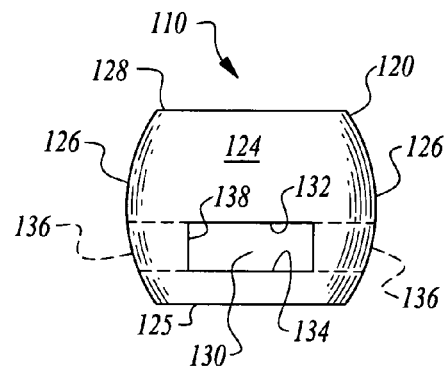
FIG. 4 is an end elevation view of that which is shown in FIG. 3.
Figure 5:
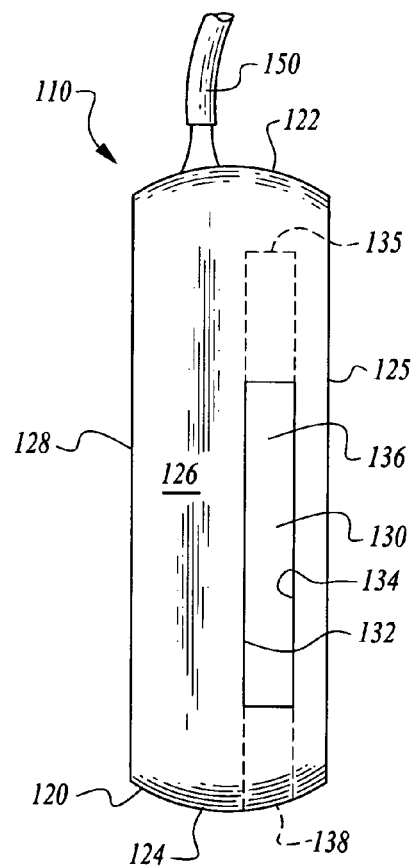
FIG. 5 is a side elevation view of that which is shown in FIG. 3.
Figures 6, 7:
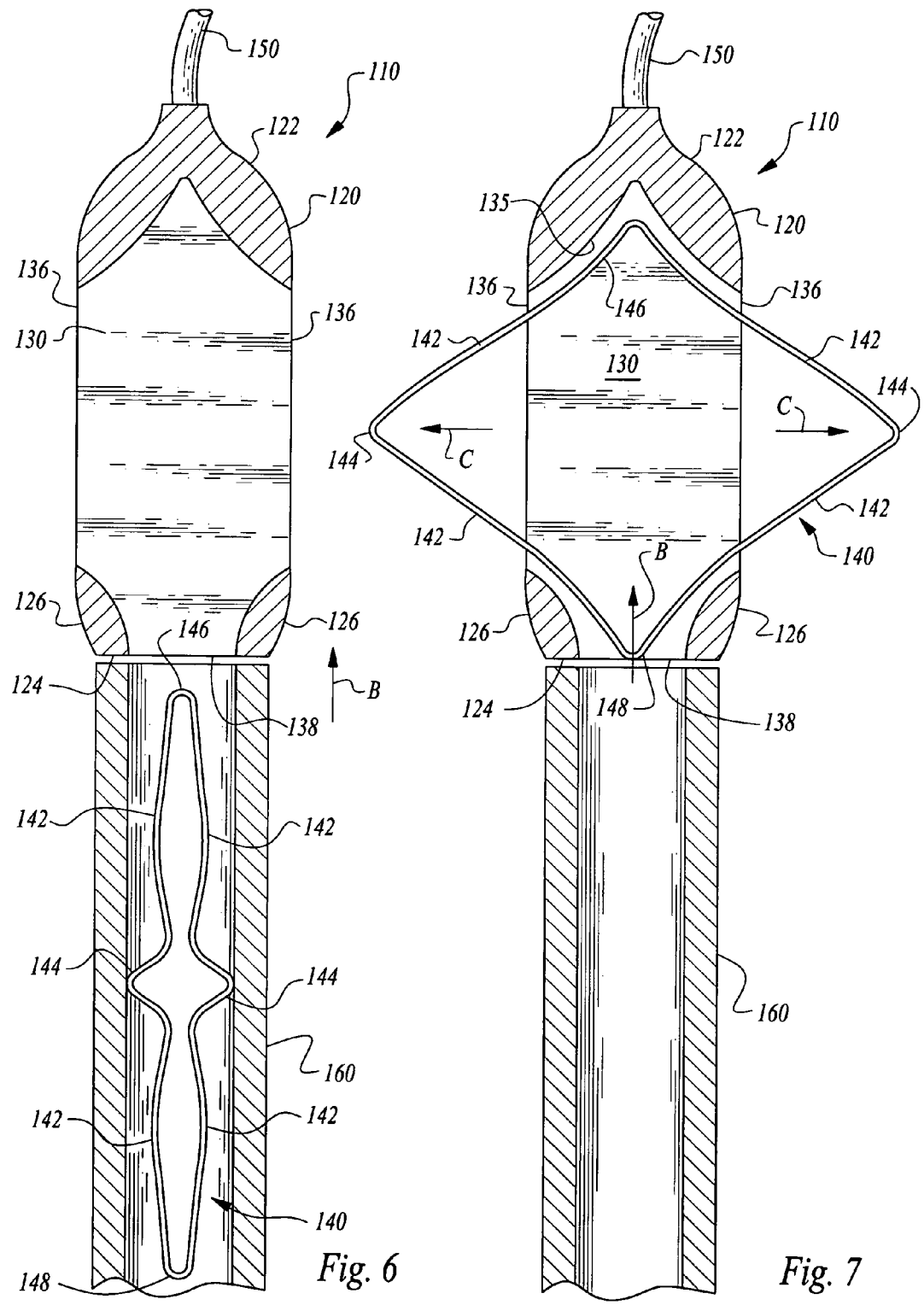
FIG. 6 is a bottom plan view of that which is shown in FIG. 3 but with a stabilizing element in the form of a loop delivered through a cannula to utilize the stabilizing element in the form of a loop that is biased toward a deployed position but retrained in a narrow configuration before insertion into the cavity of the housing.
FIG. 7 is a bottom plan view similar to that which is shown in FIG. 6 but after positioning of the stabilizing element from the cannula into the cavity.
Figure 8:
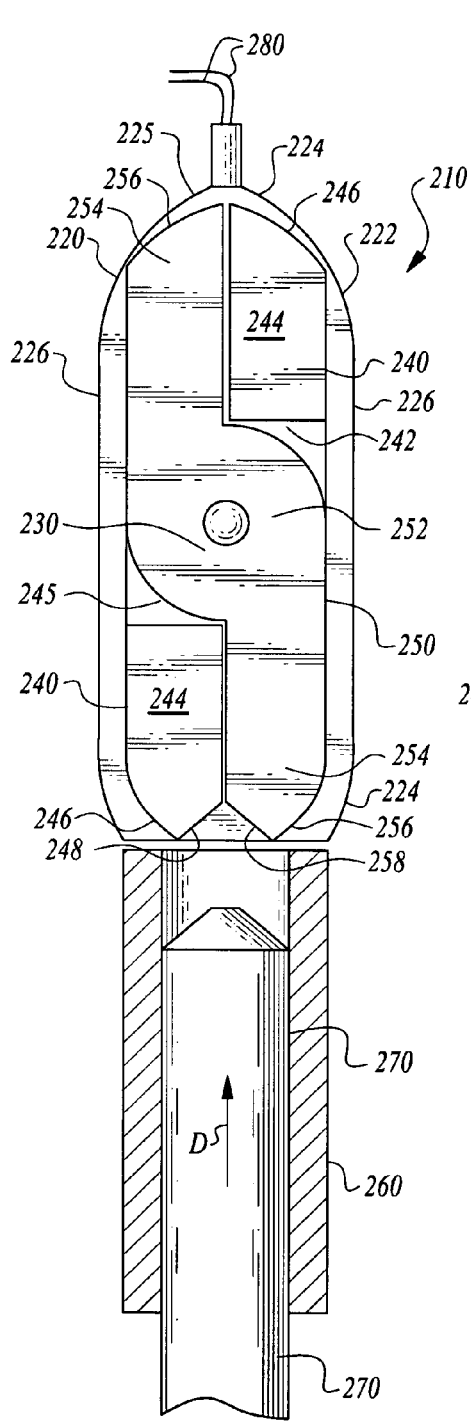
FIG. 8 is a bottom plan view of an alternative embodiment medical device and associated cannula with the medical device featuring a pair of rotating wings pivotably attached thereto and a spreader rod for use in spreading the pair of wings opposite each other for conversion of the medical device from an implantation form to a stabilized form.
Figure 9:
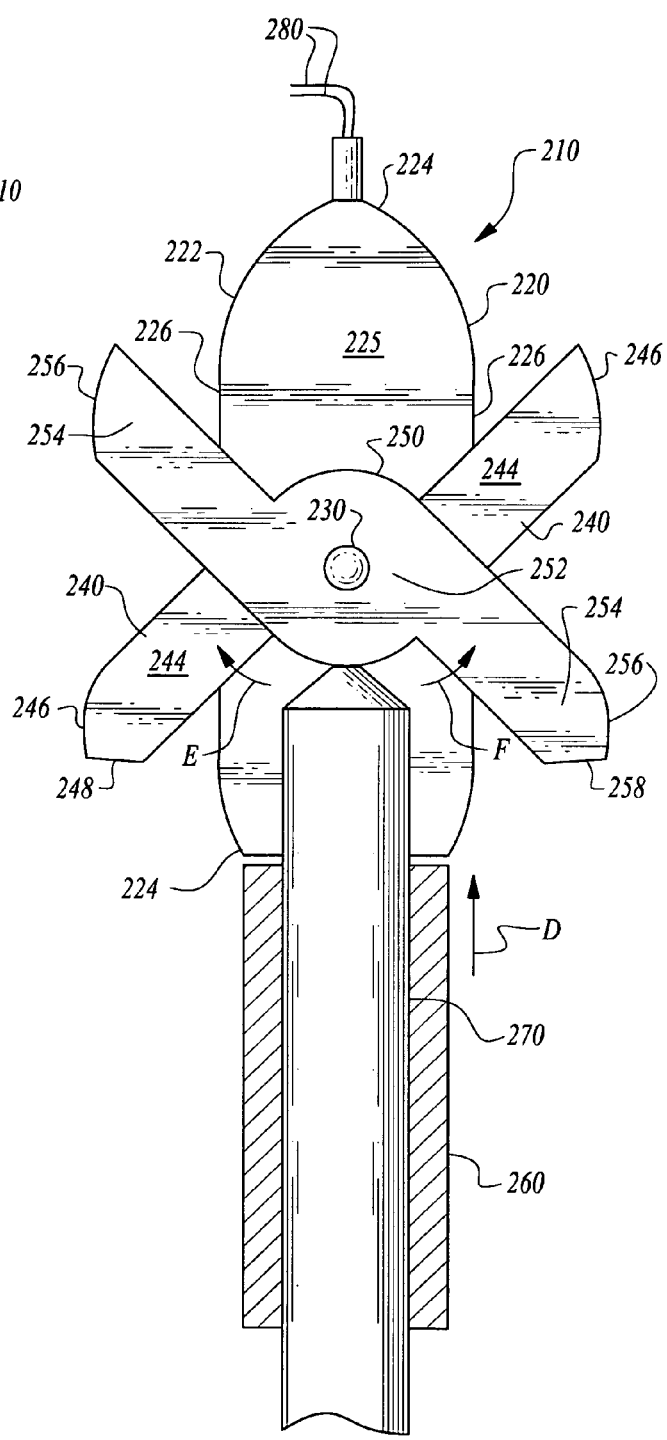
FIG. 9 is a bottom plan view similar to that which is shown in FIG. 8 but after advancing the spreader rod and rotating the wings to the final stabilized configuration.

Referring to the drawings, wherein like reference numerals represent like parts throughout the various drawing figures, reference numeral 10 (FIGS. 1 and 2) is directed to a pacemaker as one form of medical device illustrative of the enhanced stability implantable medical device of this invention. In addition to pacemakers 10, infusion pumps, ports and other medical devices could similarly be provided and utilize the same stabilization element and housing 20 as the pacemaker 10. The pacemaker 10 has an elongate form to allow it to be implanted through a small incision. A shape of the housing 20 of the pacemaker 10 is modified after arriving at the subcutaneous implantation site to enhance stability of the pacemaker 10 or other medical device implant. Two alternative embodiments are also disclosed herein including a first alternative pacemaker 110 (FIGS. 3-7) and a second alternative pacemaker 210 (FIGS. 8 and 9).

In essence, and with particular reference to FIGS. 1 and 2, basic details of the pacemaker 10 of the preferred embodiment are described. The pacemaker 10 includes at least a portion of medical device components thereof within a housing 20. The housing 20 is generally elongate in form aligned with a long axis. An axle 30 extends perpendicularly from this long axis and between sides of the housing 20. A wing 40 is pivotably attached to the housing 20, such as through the axle 30. The wing 40 can rotate between an initial position where it is aligned with the long axis of the housing 20 and a deployed form (arrow A), where it is rotated to enhance a width of the housing 20 and enhance a stability of the pacemaker 10. Electrical leads 50 are shown extending from the pacemaker 10 to output an appropriate electrical signal for heartbeat control. An outlet tube 60 is alternatively shown should the pacemaker 10 be replaced with some other medical device which delivers a fluid preparation into the body of the patient.

More specifically, and with continuing reference to FIGS. 1 and 2, specific details of the housing 20 are described according to this preferred embodiment. The housing 20 is an enclosure for at least portions of the pacemaker 10 or other medical device. Contents of the housing 20 can include a power supply, such as a battery, and appropriate control electronics for delivering an electrical signal to electrical leads 50 when specified to the heart of the patient. If an infusion pump type medical device is substituted, the housing 20 could contain a reservoir, pump elements, valves and other components typical of infusion pumps. This housing 20 is preferably substantially completely enclosed and preferably rigid in form.

The housing 20 generally includes a perimeter 22 including opposite ends 24 and opposite sides 26 extending between the ends 24. The housing 20 also includes a bottom 25 spaced from a top. The housing 20 in this preferred embodiment generally has a constant cross-section size between the bottom 25 and the top and preferably a thickness between the bottom 25 and the top that is similar to a width between the sides 26. The ends 24 and sides 26 are preferably substantially planar, but can be somewhat rounded if desired.

Importantly, the housing 20 exhibits an elongate form so that the ends 24 are spaced further from each other than a spacing between the sides 26 and a spacing between the bottom 25 and the top. Most preferably, this amount of elongation is such that a length of the housing 20 along a long axis between the ends 24 is at least about twice as great as a length of a lateral axis extending between the sides 26. The housing 20 can exhibit a greater degree of elongation with the length between the ends 24 more than twice as great as a width between the sides 26, or slightly less than this preferred amount and still benefit from the concept of this invention.

The pacemaker 10 is shown with an axle 30 extending down from the bottom 25 of the housing 20 perpendicular to the long axis and perpendicular to the lateral axis of the housing 20. While this axle 30 is not strictly required, it is beneficially provided to allow for pivotable attachment of the wing 40 to the bottom 25 of the housing 20. As an alternative to the separate axle 30, an axle-like structure can be formed into the housing 20 or the wing 40 to cooperate with a hole in the housing 20 or the wing 40. When the axle 30 is utilized, it fits within an appropriate cylindrical hole extending into the bottom 25 of the housing 20 and through the wing 40. This axle 30 is preferably cylindrical in form and has a length merely sufficient to extend a distance similar to a thickness of the wing 40.

With continuing reference to FIGS. 1 and 2, details of the wing 40 are described according to this preferred embodiment. The wing 40 is preferably a rigid structure pivotably attached to the housing 20 through the axle 30. This wing 40 preferably has a contour similar to that of the housing 20 so that the wing 40 also exhibits an elongate form. A hole 42 is provided for mounting the wing 40 to the axle 30. The wing 40 extends between opposing ends 44 with sides 46 extending between the ends 44. The sides 46 are opposite each other and define a width of the wing 40 with a length of the wing 40 defined by a distance between the ends 44. A thickness of the wing 40 is defined by a distance between a bottom 45 of the wing 40 and a top of the wing 40. The top of the wing 40 is located adjacent the bottom 25 of the housing 20.

Most preferably, the wing 40 has a perimeter size slightly less than the perimeter 22 of the housing 20. As an alternative, the wing 40 could be precisely the same perimeter size as the housing 20 or could be slightly larger than a perimeter 22 of the housing 20 and still function adequately according to this invention. Importantly, the wing 40 is preferably also elongate in form with a length about twice (or more) that of a width thereof.

The wing 40 is adapted to rotate relative to the housing 20 (along arrow A of FIGS. 1 and 2). This rotation allows the wing 40 to change from an implantation configuration to a deployed configuration for the housing 20, so that the housing 20 goes from having an elongate low profile form, such as while being passed through a small incision, to a large stable platform once implanted. This minimizes the possibility of "Twiddler's Syndrome" or other undesirable movement of the pacemaker 10 or other medical device once implanted.

Electrical leads 50 or outlet tubes 60 preferably extend from one of the ends 24 of the housing 20 or some other portion of the housing 20. To keep the wing 40 in its deployed position, it is conceivable that the bottom 25 of the housing 20 and the top of the wing 40 could be configured so that they include appropriate detent structures so that the wing 40 snaps into a final deployed position once rotated relative to the housing 20. Alternatively, holes can be formed in the housing 20 and the wing 40 which can receive sutures to tie the wing 40 in its open position relative to the housing 20.

Should the pacemaker 10 or other medical device require removal, the wing 40 can merely be rotated back to its implantation position by overcoming forces associated with the detents in the wing 40 and the housing 20, or by severing sutures to allow the wing 40 to freely rotate back to its implantation position with a long axis of the wing 40 aligned with a long axis of the housing 20. Whenever such implantation or removal occurs, a relatively small incision is required to pass through the skin and yet a stable medical device is still provided.

While the wing 40 is shown as a preferred form of stabilizing element, other forms of stabilizing elements could also be utilized including spring loaded stabilizing elements which automatically deploy after passing through the skin or reaching the incision site. Also, the wing 40 could be in the form of a pair of wings (FIGS. 8 and 9) or could be a structure having a form generally that of a "T" or "V" which either rotates relative to the housing 20 or is spring loaded to deploy arms to enhance a width of the medical device after complete implantation.

The wing 40 can be rotated after the medical device has reached the implantation site or immediately after passing through an incision in the skin. Such rotation can occur manually, such as through use of an appropriate probe or manipulation with the fingers. Most preferably, such rotation is achieved through use of a spring that biases the wing 40 to its deployed position extending laterally from the housing 20 long axis. Such a spring can be a torsion spring adjacent the axle 30 and contained within a recess in the wing 40 adjacent the axle 30, and/or a recess in the bottom of the housing 20 adjacent the axle 30. The spring could be formed of a biocompatible metal such as titanium (or alloys thereof) or made of a biocompatible plastic or other other non-metal material. The spring could also be a linear compression spring or other linear force applying spring located further from the axle 30 and interposed between the wing 40 and the housing 20. With such a spring, the wing 40 is both advanced to the deployed configuration and held in the deployed configuration after rotation. Further support in the deployed position can be provided by detents or suturing also.

With particular reference to FIGS. 3-7, details of the first alternative pacemaker 110 are described. The pacemaker 110 includes a housing 120 with a general elongate form similar to that of the housing 20. Thus, the housing 120 includes a front end 122 opposite a rear end 124 with sides 126 extending between the front end 122 and rear end 124. A thickness of the housing 120 is defined as a distance between the bottom 125 and top 128.

Uniquely, the housing 120 includes a cavity 130 therein. Preferably, this cavity 130 is closer to the bottom 125 than to the top 128 and has a planar form within a plane perpendicular to a vertical axis and aligned with both a long axis and a lateral axis for the housing 120. A long axis is defined as an axis extending from the front end 122 to the rear end 124 and the lateral axis is defined as an axis extending between the sides 126. The cavity 130 includes a roof 132 which is planar in form and spaced a constant distance away from a floor 134. An abutment wall 135 defines a wall extending from the roof 132 to the floor 134 on a side of the cavity 130 adjacent the front end 122 of the housing 120. The cavity 130 also includes side openings 136 extending out sides 126 of the housing 120 and a rear opening 138 extending out of the rear end 124 of the housing 120.

A loop 140 is provided as a preferred form of stabilizing element which can reside within the cavity 130 and extend laterally out of at least one of the side openings 136 and preferably both of the side openings 136 to stabilize the housing 120 after implantation. The loop 140 in this preferred form shown includes four legs 142 joined together by a front joint 146, side joints 144 and a rear joint 148. The front joint 146 is located adjacent the abutment wall 135. The rear joint 148 is adjacent the rear opening 134. The side joints 144 are adjacent the side openings 136. The loop 140 is sized so that the side joints 144 extend out of the side openings 136 and enhance an effective width and footprint of the housing 120 of the first alternative pacemaker 110. An interface port 150 extends from the housing 120 which can be in the form of electric leads or a fluid tube depending on the type of medical device provided, such as the pacemaker 110.

While a continuous loop 140 is shown, other stabilizing elements could be provided of similar form but not a complete loop. For instance, any one of the joints might be omitted so that adjacent legs 142 end at free ends, and such a modified loop would still function somewhat effectively.

The loop 140 can be deployed a variety of different ways relative to the cavity 130 of the housing 120. In one embodiment the loop 140 can be provided within the cavity 130 during implantation. The loop 140 can be sufficiently flexible that as the pacemaker 110 is advanced through an incision, the side joints 144 are merely flexed towards each other as they pass through the incision. The loop 140 would be formed of a resilient material so that the side joints 144 would spring to a natural original position (along arrow C of FIGS. 3 and 7) once reaching the implantation site.

Alternatively, the loop 140 could be formed of a plastically deformable material, such as a surgical stainless steel with thin cross-section legs 142 and initially reside within the cavity 130, but passing out of the rear opening 138 somewhat and not passing out of the side openings 136. After reaching the implantation site, the rear joint 148 would be advanced toward the front joint 146 and the loop 140 would be caused to bend so that the side joints 144 would bend away from each other and out of the side openings 136.

As another alternative, the loop 140 could be formed as bendable material but be advanced later, such as through a cannula (along arrow B of FIGS. 3, 6 and 7), until the front joint 146 abuts the abutment wall 135 and then with further advancing of the loop 140 is caused to bend so the side joints 144 extend out the side openings 136 of the cavity 130. Also, the loop 140 could be formed of a resilient material, such as nickel titanium and still advance (arrow B) through a catheter/cannula 160 that would initially restrain the loop 140 to have an elongate form (FIG. 6) and after advancing into the cavity 130 would be allowed to attain its natural original form (arrow C) deployed into a generally diamond shape (FIG. 7) to provide the stable enhanced width footprint for the pacemaker 110 or other medical device, once at the implantation site.

With particular reference to FIGS. 8 and 9, details of a second alternative pacemaker 210 or other medical device are disclosed. This second alternative pacemaker 210 has a housing 220 similar to the housing 20 of the preferred embodiment (FIGS. 1 and 2). Thus, the housing 220 includes a perimeter 222 defined by ends 224 at opposite ends of a long axis and sides 226 extending between the ends 224 and defining a lateral axis extending therebetween. The housing 220 also includes a top opposite a bottom 225 defining a thickness of the housing 220. Electric leads 280 or other output extends from the housing 220. An axle 230 extends from the bottom 225 of the housing 220 in a most preferred form of this second alternative pacemaker or other medical device.

Uniquely, a pair of wings 240, 250 are pivotally attached to the axle 230 of the housing 220. In particular, these wings 240, 250 include a top wing 240 and a bottom wing 250. The top wing 240 is closer to the bottom 225 of the housing 220 and includes a hub 242 adjacent the axle 230 with a hole therein that allows the top wing 240 to be mounted to the axle 230. Arms 244 extend in opposite directions away from the hub 242 to tips 246. A recess 245 is provided adjacent the hub 242 into which the bottom wing 250 can partially reside so that the top wing 240 and bottom wing 250 can remain within a substantially common plane with each other both before and after rotation thereof. Preferably, at least one of the tips 246 of the top wing 240 includes a bevel 248 thereon on a portion of the top wing 240 which extends most rearwardly on the top wing 240.

The bottom wing 250 includes a hub 252 adapted to be mounted on the axle 230 and adapted to reside within the recess 245 in the top wing 240. The bottom wing 250 is most distant from the bottom 225 of the housing 220. Arms 254 extend in opposite directions away from the hub 252 to tips 256. Preferably, at least one of the tips 256 includes a bevel 258 thereon on a portion of one of the arms 254 which extends most rearwardly. This bevel 258 preferably at least partially faces the bevel 248 of the top wing 240.

The wings 240, 250 are each adapted to rotate relative to each other and relative to the housing 220 (arrows E and F). Initially, the wings 240, 250 reside substantially within a perimeter 222 of the housing 220. After rotation (along arrows E and F) the wings 240, 250 extend outside this perimeter 222 of the housing 220 to enhance the stability of the pacemaker 210 or other alternative medical device.

Preferably, a cannula 260 can be placed adjacent the pacemaker 210 and a spreader rod 270 can be advanced through the cannula 260 and pressed between the bottom wing 250 and top wing 240. The spreader rod 270 can press against the bevel 248 and bevel 258 to cause simultaneous rotation of the top wing 240 and bottom wing 250 in opposite directions relative to each other and relative to the housing 220. Such rotation preferably occurs for at least 45° so that the wings 240, 250 form an "X." A rather desirable stabilized form would involve rotation of 60° so that the wings 240, 250 and ends 224 of the housing 220 would define six peripheral ends for the overall final implanted pacemaker 210 or other implanted medical device. Advancement of the spreader rod 270 along arrow D (FIGS. 8 and 9) allows for such rotation (along arrows E and F) for rotation of the wings 240, 250 from an implantation position to a deployed position.

The medical device 210 can have the pair of wings advanced and held in the deployed position by action of a spring, similar to that described in conjunction with the embodiment of FIGS. 1 and 2 above. With two wings, the spring can act between the springs or two springs can be provided, each acting between the housing and one of the wings.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A shape variable medical device for implantation subcutaneously, the medical device comprising in combination:
    a housing;
    said housing having an elongate form between a front end and a rear end;
    said housing having a long dimension extending from said front end to said rear end along a long axis;
    said housing having a lateral dimension extending along a lateral axis non-parallel with said long axis;
    said lateral dimension having a length less than a length of said long dimension;
    at least one stabilizing element;
    said stabilizing element pivotably attached to said housing;
    said stabilizing element having an elongate form extending between ends thereof;
    said ends of said stabilizing element joined together by sides extending between said ends and on opposite portions of said stabilizing element;
    said sides of said stabilizing element longer than said ends of said stabilizing element;
    said sides of said stabilizing element having a length longer than a length of said lateral dimension, such that when said stabilizing element is rotated from a first position more aligned with said long axis to a second position more aligned with said lateral axis, said stabilizing element extends laterally from said housing to stabilize said housing; and
    wherein an axle is provided extending non-parallel with said long dimension of said housing, said stabilizing element pivotably attached to said housing through said axle.

2. A shape variable medical device for implantation subcutaneously, the medical device comprising in combination:
    a housing;
    said housing having an elongate form between a front end and a rear end;
    said housing having a long dimension extending from said front end to said rear end along a long axis;
    said housing having a lateral dimension extending along a lateral axis non-parallel with said long axis;
    said lateral dimension having a length less than a length of said long dimension;
    at least one stabilizing element;
    said stabilizing element pivotably attached to said housing;
    said stabilizing element having an elongate form extending between ends thereof;
    said ends of said stabilizing element joined together by sides extending between said ends and on opposite portions of said stabilizing element;
    said sides of said stabilizing element longer than said ends of said stabilizing element;
    said sides of said stabilizing element having a length longer than a length of said lateral dimension, such that when said stabilizing element is rotated from a first position more aligned with said long axis to a second position more aligned with said lateral axis, said stabilizing element extends laterally from said housing to stabilize said housing; and
    wherein an axle extends non-parallel with said long axis from a bottom of said housing, said stabilizing element pivotably attached to said axle.

3. The medical device of claim 2 wherein said stabilizing element has a shape similar to that of a perimeter of said housing, such that said stabilizing element remains substantially within a perimeter of said housing when said stabilizing element has said ends of said stabilizing element aligned with said long axis of said housing.

4. The medical device of claim 2 wherein said stabilizing element is adapted to rotate at least about 45° relative to said housing.

5. The medical device of claim 2 wherein a detent snap assembly is formed into said stabilizing element and said housing to cause said stabilizing element to tend to remain in a deployed position after rotation to said deployed position to maintain stability for said medical device.

6. The medical device of claim 2 wherein said housing and said stabilizing element include holes therein, said holes adapted to receive sutures passing therethrough to secure said stabilizing element in a deployed orientation rotated away from alignment with said perimeter of said housing to maintain stability of said medical device after implantation.

7. The medical device of claim 2 wherein electric leads extend from said housing and said housing contains at least portions of a cardiac rhythm manager therein, such that said medical device is in the form of a cardiac rhythm manager.

8. A medical device adapted to be implanted subcutaneously and to morph between a lower profile dynamic form and a higher profile static form, the medical device comprising in combination:
    a housing;
    said housing adapted to contain at least a portion of a medical device therein for treatment of a patient into which the medical device is implanted;
    said housing having an elongate form with a lateral width lesser than a long axis length thereof;
    said long axis length non-parallel with said lateral width;
    a stabilizing element interfacing with said housing;
    wherein an axle is provided extending non-parallel with said long axis length of said housing, said stabilizing element pivotably attached to said housing through said axle; and
    said stabilizing element adapted to be affixed to said housing and adjusted to exhibit a width greater than said lateral width of said housing when said stabilizing element is transitioned from a lower profile dynamic form for the medical device to a higher profile static form for the medical device.

9. The medical device of claim 8 wherein said stabilizing element has a length between ends thereof at least as great as said long axis length of said housing.

10. The medical device of claim 8 wherein said stabilizing element is adapted to rotate relative to said housing to transition said stabilizing element from the lower profile dynamic position to the higher profile static position.

11. The medical device of claim 10 wherein said stabilizing element is in the form of a wing having an elongate form extending between ends thereof.

12. The medical device of claim 11 wherein said wing has a contour similar to the contour of said housing with said wing adapted to rotate at least about 45° from the lower profile dynamic position to the higher profile static position for said wing.

13. The medical device of claim 11 wherein a pair of wings are provided, each of said wings adapted to rotate in opposite directions relative to said housing, said pair of wings having similar lengths extending between ends thereof, with rear most ends of said pair of wings having beveled surfaces thereon at least partially facing each other, such that a spreader rod can be inserted between said beveled surfaces and cause rotation of said wings in opposite directions away from said spreader rod upon impacting each of said beveled surfaces.

14. The medical device of claim 8 wherein said housing includes electrical leads extending therefrom and said housing includes at least portions of a cardiac rhythm manager therein, such that the medical device is in the form of a cardiac rhythm manager.

* * * * *